United States Patent
Itkowitz et al.

(10) Patent No.: US 12,164,684 B2
(45) Date of Patent: Dec. 10, 2024

(54) GAZE-INITIATED COMMUNICATIONS

(71) Applicant: INTUITIVE SURGICAL OPERATIONS, INC., Sunnyvale, CA (US)

(72) Inventors: Brandon D. Itkowitz, San Jose, CA (US); Joseph M. Arsanious, Riverside, CA (US); Christopher R. Burns, San Jose, CA (US); Heath Feather, Cupertino, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 0 days.

(21) Appl. No.: 18/340,701

(22) Filed: Jun. 23, 2023

(65) Prior Publication Data

US 2023/0400920 A1 Dec. 14, 2023

Related U.S. Application Data

(63) Continuation of application No. 16/391,981, filed on Apr. 23, 2019, now Pat. No. 11,726,559.

(Continued)

(51) Int. Cl.
*G06F 3/01* (2006.01)
*G06F 3/04817* (2022.01)
(Continued)

(52) U.S. Cl.
CPC .......... *G06F 3/013* (2013.01); *G06F 3/04817* (2013.01); *G06F 3/167* (2013.01); *G16H 80/00* (2018.01)

(58) Field of Classification Search
CPC ...... G06F 3/013; G06F 3/04817; G06F 3/167; G06F 2203/0381; G16H 80/00; G16H 20/40; G16H 40/67
See application file for complete search history.

(56) References Cited

U.S. PATENT DOCUMENTS 5,880,731 A  3/1999 Liles et al.
10,278,782 B2  5/2019 Jarc et al.
(Continued)

OTHER PUBLICATIONS

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

*Primary Examiner* — Andrey Belousov
(74) *Attorney, Agent, or Firm* — Haynes & Boone, LLP.

(57) ABSTRACT

A system comprises a display configured to present a graphical user interface including a viewing area and one or more user interface elements. The system also comprises a gaze tracking device configured to detect a change in a gaze of a user while the user views the graphical user interface presented on the display. The system also comprises an audio input device configured to receive audio information. The system also comprises one or more processors configured to process the audio information received at the audio input device in accordance with a first mode to direct the received audio information as audio output to one or more audio output devices; and in response to the gaze tracking device detecting the change in the gaze of the user, process the received audio information in accordance with a second mode, the second mode being distinct from the first mode.

20 Claims, 9 Drawing Sheets

Related U.S. Application Data

(60) Provisional application No. 62/661,979, filed on Apr. 24, 2018.

(51) Int. Cl.
*G06F 3/16* (2006.01)
*G16H 80/00* (2018.01)

(56) References Cited

U.S. PATENT DOCUMENTS

| | | |
|---|---|---|
| 2006/0095848 A1 | 5/2006 | Naik |
| 2007/0208806 A1* | 9/2007 | Mordecai .............. G06Q 10/10 709/204 |
| 2009/0007016 A1 | 1/2009 | Lindberg et al. |
| 2010/0226100 A1 | 9/2010 | Johnson et al. |
| 2014/0282196 A1* | 9/2014 | Zhao ..................... G06F 3/013 715/771 |
| 2015/0049163 A1 | 2/2015 | Smurro |
| 2015/0077502 A1 | 3/2015 | Jordan et al. |
| 2016/0195924 A1 | 7/2016 | Weber et al. |
| 2019/0113969 A1 | 4/2019 | Borge et al. |
| 2019/0324533 A1 | 10/2019 | Itkowitz et al. |

\* cited by examiner

GAZE-INITIATED COMMUNICATIONS

CROSS-REFERENCE TO RELATED APPLICATIONS

This application is a continuation of U.S. patent application Ser. No. 16/391,981 (now U.S. Pat. No. 11,726,559) filed Apr. 23, 2019, which claims the benefit of U.S. Provisional Application No. 62/661,979 filed Apr. 24, 2018, all of which are incorporated by reference herein in their entirety.

FIELD

The present disclosure is directed to managing medical systems and, more particularly, to systems and methods for initiating communications with medical systems using gaze.

BACKGROUND

Minimally invasive medical techniques are intended to reduce the amount of extraneous tissue that is damaged during diagnostic or surgical procedures, thereby reducing patient recovery time, discomfort, and harmful side effects. Such minimally invasive techniques may be performed through natural orifices in a patient anatomy or through one or more surgical incisions. Through these natural orifices or incisions, clinicians may insert medical tools to reach a target tissue location. Minimally invasive medical tools include instruments such as therapeutic instruments, diagnostic instruments, and surgical instruments. Minimally invasive medical tools may also include imaging instruments such as endoscopic instruments that provide a user with a field of view within the patient anatomy.

Some minimally invasive medical tools may be teleoperated, otherwise remotely operated, or otherwise computer-assisted. A clinician may need to be able to communicate with a teleoperational system as well as other systems in a surgical environment before, during, or after a medical procedure performed with the teleoperational system. Still further, a clinician may need to be able to easily communicate with other members of the clinical team in a surgical environment before, during, or after a medical procedure. Systems and methods for improving the process by which medical personnel communicate with each other and with systems in a surgical environment are needed.

SUMMARY

The embodiments of the invention are summarized by the claims that follow the description.

In one embodiment, a method is provided for gaze-initiated communications. A gaze of a user is detected being directed at an element in a graphical user interface. The graphical user interface is displayed on a display system located in an environment. A state of the element is changed in response to detecting that the gaze is directed at the element. Audio information is received through an audio input device. An output operation is controlled based on the state of the element such that the audio information received through the audio input device is directed to an information conveyor corresponding to the element.

In another embodiment, a method for selectively communicating audio information using gaze is provided. A gaze of a user is detected being directed at an element in a graphical user interface. The graphical user interface is displayed on a display system located in an environment and wherein the element is associated with at least one communication channel. A state of the element is changed to a listening state in response to detecting that the gaze is directed at the element. A visual cue is presented in the graphical user interface indicating that the element is now in the listening state. Audio information is received through an audio input device. The audio information received through the audio input device is directed to the at least one communication channel associated with the element while the element is in the listening state.

In yet another embodiment, a method for selectively controlling a plurality of systems using voice commands is provided. A gaze of a user is detected being directed at an element in a graphical user interface. The graphical user interface is displayed on a display system located in an environment and wherein the element represents a system. Audio information is received through an audio input device. The audio input device is directed to an information conveyor dedicated to receiving voice commands for the system represented by the element. Speech recognition context information designated for the system represented by the element is selected for use in processing the audio information. The audio information is processed using the speech recognition context information to generate output information that is used to control an operation of the system represented by the element.

In another embodiment, an apparatus comprises a display system, a gaze tracking system, an audio input device, and a processor. The display system is located in an environment and configured to display a graphical user interface that includes a plurality of elements. The gaze tracking system is configured to detect a gaze of a user that is directed at an element of the plurality of elements in the graphical user interface. The audio input device is configured to receive audio information. The processor is configured to change a state of the element in response to detecting that the gaze is directed at the element and to control an output operation based on the state of the element such that the audio information received through the audio input device is directed to an information conveyor corresponding to the element.

It is to be understood that both the foregoing general description and the following detailed description are exemplary and explanatory in nature and are intended to provide an understanding of the present disclosure without limiting the scope of the present disclosure. In that regard, additional aspects, features, and advantages of the present disclosure will be apparent to one skilled in the art from the following detailed description.

BRIEF DESCRIPTIONS OF THE DRAWINGS

Aspects of the present disclosure are best understood from the following detailed description when read with the accompanying figures. It is emphasized that, in accordance with the standard practice in the industry, various features are not drawn to scale. In fact, the dimensions of the various features may be arbitrarily increased or reduced for clarity of discussion. In addition, the present disclosure may repeat reference numerals and/or letters in the various examples. This repetition is for the purpose of simplicity and clarity and does not in itself dictate a relationship between the various embodiments and/or configurations discussed.

DETAILED DESCRIPTION

Figure 1A:
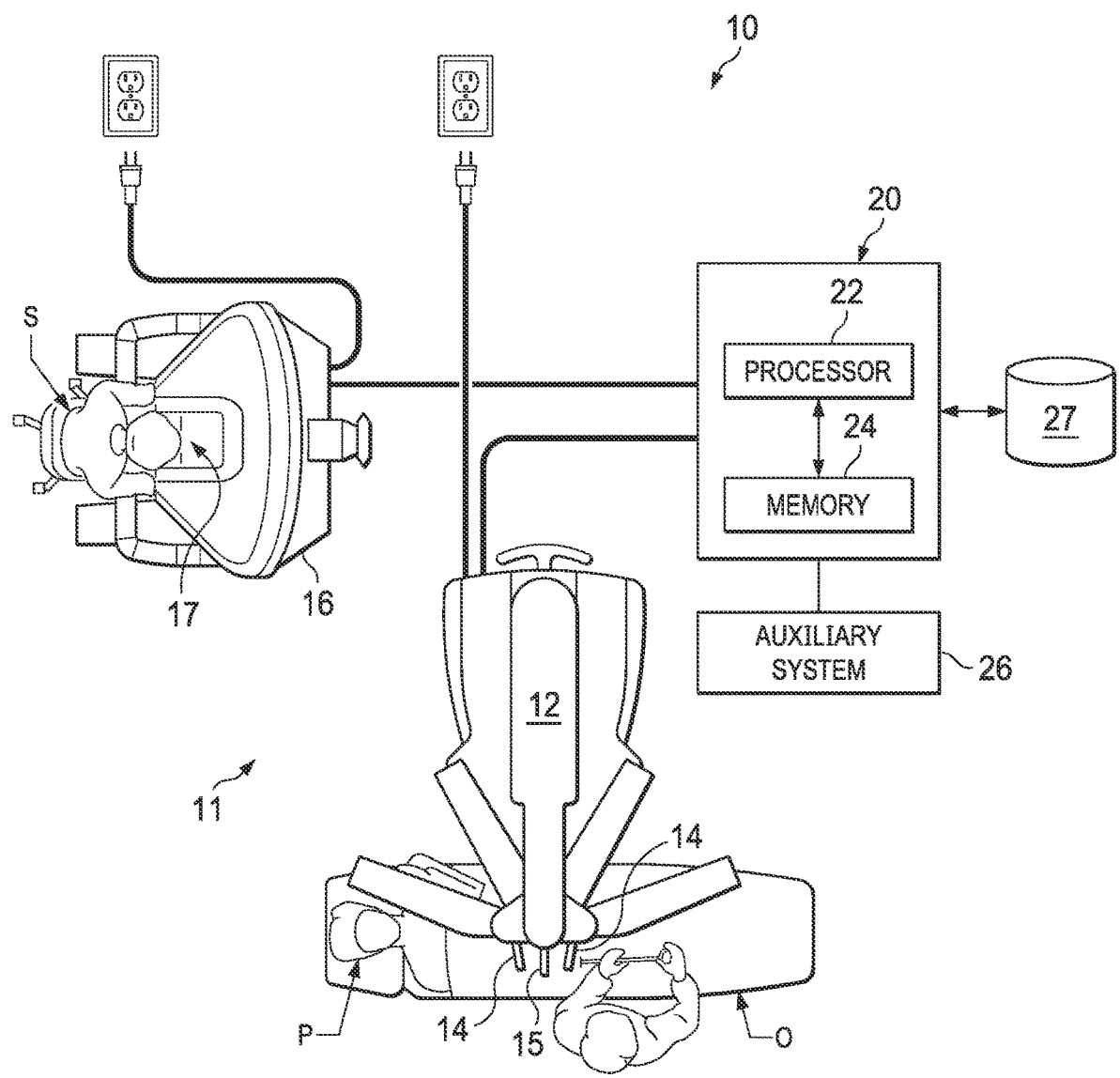
FIG. 1A is a schematic view of a medical system, in accordance with an embodiment.

For the purposes of promoting an understanding of the principles of the present disclosure, reference will now be made to the embodiments illustrated in the drawings, and specific language will be used to describe the same. It will nevertheless be understood that no limitation of the scope of the disclosure is intended. In the following detailed description of the aspects of the invention, numerous specific details are set forth in order to provide a thorough understanding of the disclosed embodiments. However, as would be appreciated by one skilled in the art, embodiments of this disclosure may be practiced without these specific details. In other instances well known methods, procedures, components, and circuits have not been described in detail so as not to unnecessarily obscure aspects of the embodiments of the invention.

Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one embodiment may be combined with the features, components, and/or steps described with respect to other embodiments of the present disclosure. In addition, dimensions provided herein are for specific examples and it is contemplated that different sizes, dimensions, and/or ratios may be utilized to implement the concepts of the present disclosure. To avoid needless descriptive repetition, one or more components or actions described in accordance with one illustrative embodiment may be used or omitted as applicable from other illustrative embodiments. For the sake of brevity, the numerous iterations of these combinations will not be described separately. For simplicity, in some instances the same reference numbers are used throughout the drawings to refer to the same or like parts.

The embodiments below will describe various instruments and portions of instruments in terms of their state in three-dimensional space. As used herein, the term "position" refers to the location of an object or a portion of an object in a three-dimensional space (e.g., three degrees of translational freedom along Cartesian X, Y, Z coordinates). As used herein, the term "orientation" refers to the rotational placement of an object or a portion of an object (three degrees of rotational freedom—e.g., roll, pitch, and yaw). As used herein, the term "pose" refers to the position of an object or a portion of an object in at least one degree of translational freedom and to the orientation of that object or portion of the object in at least one degree of rotational freedom (up to six total degrees of freedom).

Figure 1B:
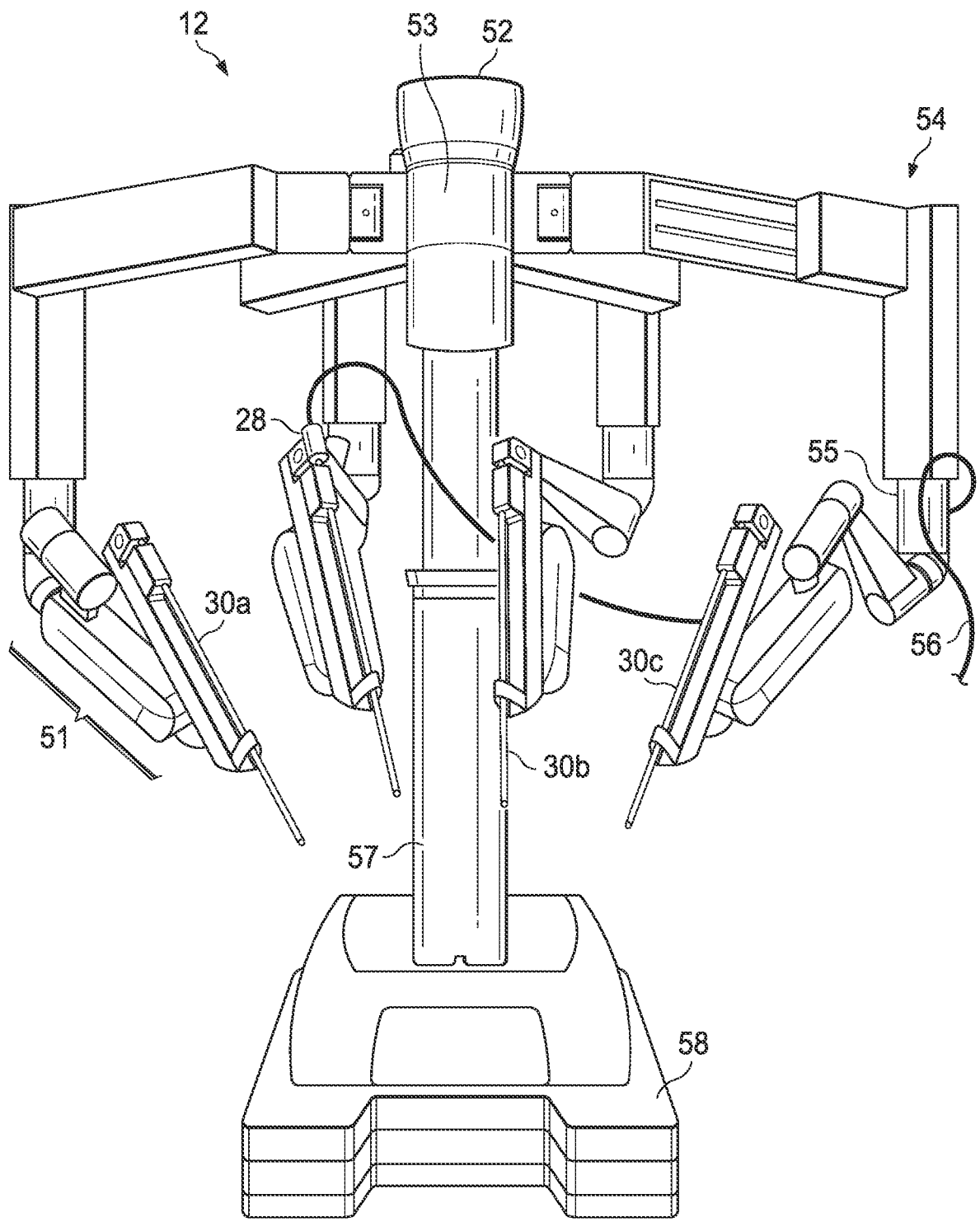
FIG. 1B is a perspective view of an assembly, in accordance with an embodiment.
Figure 1C:
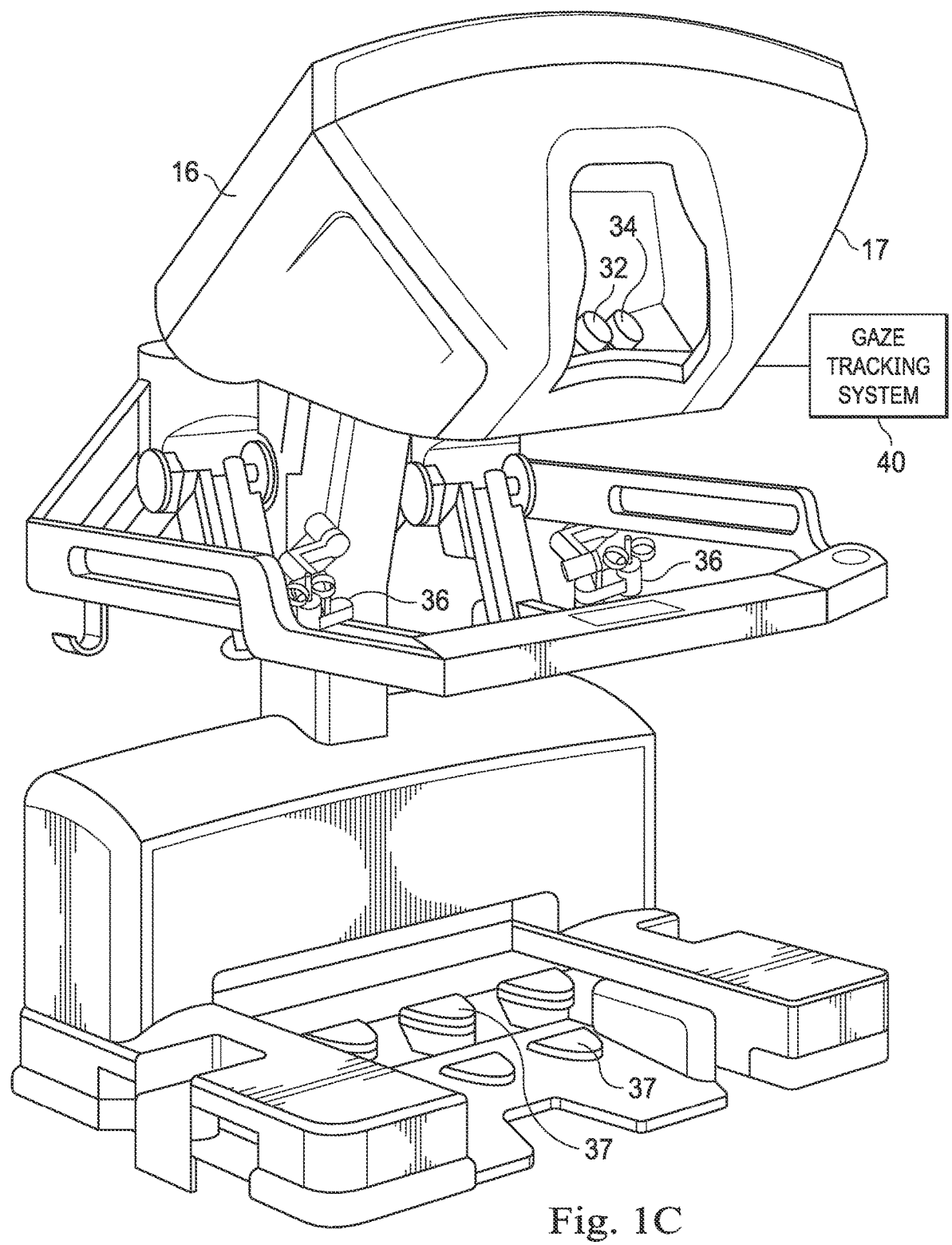
FIG. 1C is a perspective view of a surgeon's control console for a medical system, in accordance with an embodiment.

Referring now to the drawings, FIGS. 1A, 1B, and 1C together provide a schematic overview of a medical system 10 that may be used in, for example, medical procedures including diagnostic, therapeutic, or surgical procedures. The medical system 10 is located in a surgical environment 11. In one or more embodiments, the medical system 10 may be a teleoperational medical system that is under the teleoperational control of a surgeon. In alternative embodiments, the medical system 10 may be under the partial control of a computer programmed to perform the medical procedure or sub-procedure. In still other alternative embodiments, the medical system 10 may be a fully automated medical system that is under the full control of a computer programmed to perform the medical procedure or sub-procedure with the medical system 10. One example of the medical system 10 that may be used to implement the systems and techniques described in this disclosure is the da Vinci® Surgical System manufactured by Intuitive Surgical, Inc. of Sunnyvale, California.

As shown in FIG. 1A, the medical system 10 generally includes an assembly 12, which may be mounted to or positioned near an operating table O on which a patient P is positioned. The assembly 12 may be referred to as a patient side cart, a surgical cart, or a surgical robot. In one or more embodiments, the assembly 12 may be a teleoperational assembly. The teleoperational assembly may be referred to as, for example, a teleoperational arm cart. A medical instrument system 14 and an endoscopic imaging system 15 are operably coupled to the assembly 12. An operator input system 16 allows a surgeon or other type of clinician S to view images of or representing the surgical site and to control the operation of the medical instrument system 14 and/or the endoscopic imaging system 15.

The medical instrument system 14 may comprise one or more medical instruments. In embodiments in which the medical instrument system 14 comprises a plurality of medical instruments, the plurality of medical instruments may include multiple of the same medical instrument and/or multiple different medical instruments. Similarly, the endoscopic imaging system 15 may comprise one or more endoscopes. In the case of a plurality of endoscopes, the plurality of endoscopes may include multiple of the same endoscope and/or multiple different endoscopes.

The operator input system 16 may be located at a surgeon's control console 17 and may be located in the same room as operating table O. In some embodiments, the surgeon S and the operator input system 16 may be located in a different room or a completely different building from the patient P. The operator input system 16 generally includes one or more control device(s) for controlling the medical instrument system 14. The control device(s) may include one or more of any number of a variety of input devices, such as hand grips, joysticks, trackballs, data gloves, trigger-guns, foot pedals, hand-operated controllers, voice recognition devices, touch screens, body motion or presence sensors, and other types of input devices.

In some embodiments, the control device(s) will be provided with the same degrees of freedom as the medical instrument(s) of the medical instrument system 14 to provide the surgeon with telepresence, which is the perception that the control device(s) are integral with the instruments so that the surgeon has a strong sense of directly controlling instruments as if present at the surgical site. In other embodiments, the control device(s) may have more or fewer degrees of freedom than the associated medical instruments and still provide the surgeon with telepresence. In some embodiments, the control device(s) are manual input devices that move with six degrees of freedom, and which may also include an actuatable handle for actuating instruments (for example, for closing grasping jaw end effectors, applying an electrical potential to an electrode, delivering a medicinal treatment, and actuating other types of instruments).

The assembly 12 supports and manipulates the medical instrument system 14 while the surgeon S views the surgical site through the operator input system 16. An image of the surgical site may be obtained by the endoscopic imaging system 15, which may be manipulated by the assembly 12. The assembly 12 may comprise endoscopic imaging systems 15 and may similarly comprise multiple medical instrument systems 14 as well. The number of medical instrument systems 14 used at one time will generally depend on the diagnostic or surgical procedure to be performed and on space constraints within the operating room, among other factors. The assembly 12 may include a kinematic structure of one or more non-servo controlled links (e.g., one or more links that may be manually positioned and locked in place, generally referred to as a set-up structure) and a manipulator. When the manipulator takes the form of a teleoperational manipulator, the assembly 12 is a teleoperational assembly. The assembly 12 includes a plurality of motors that drive inputs on the medical instrument system 14. In an embodiment, these motors move in response to commands from a control system (e.g., control system 20). The motors include drive systems which when coupled to the medical instrument system 14 may advance a medical instrument into a naturally or surgically created anatomical orifice. Other motorized drive systems may move the distal end of said medical instrument in multiple degrees of freedom, which may include three degrees of linear motion (e.g., linear motion along the X, Y, Z Cartesian axes) and three degrees of rotational motion (e.g., rotation about the X, Y, Z Cartesian axes). Additionally, the motors may be used to actuate an articulable end effector of the medical instrument for grasping tissue in the jaws of a biopsy device or the like. Medical instruments of the medical instrument system 14 may include end effectors having a single working member such as a scalpel, a blunt blade, an optical fiber, or an electrode. Other end effectors may include, for example, forceps, graspers, scissors, or clip appliers.

The medical system 10 also includes a control system 20. The control system 20 includes at least one memory 24 and at least one processor 22 for effecting control between the medical instrument system 14, the operator input system 16, and other auxiliary systems 26 which may include, for example, imaging systems, audio systems, fluid delivery systems, display systems, illumination systems, steering control systems, irrigation systems, and/or suction systems. A clinician C may circulate within the surgical environment 11 and may access, for example, the assembly 12 during a set up procedure or view a display of the auxiliary system 26 from the patient bedside.

Though depicted as being external to the assembly 12 in FIG. 1A, the control system may, in some embodiments, be contained wholly within the assembly 12. The control system also includes programmed instructions (e.g., stored on a non-transitory, computer-readable medium) to implement some or all of the methods described in accordance with aspects disclosed herein. While the control system 20 is shown as a single block in the simplified schematic of FIG. 1A, the control system 20 may include two or more data processing circuits with one portion of the processing optionally being performed on or adjacent the assembly 12, another portion of the processing being performed at the operator input system 16, and the like.

Any of a wide variety of centralized or distributed data processing architectures may be employed. Similarly, the programmed instructions may be implemented as a number of separate programs or subroutines, or they may be integrated into a number of other aspects of the systems described herein, including teleoperational systems. In one embodiment, the control system 20 supports wireless communication protocols such as Bluetooth, IrDA, HomeRF, IEEE 802.11, DECT, and Wireless Telemetry.

The control system 20 is in communication with a database 27 which may store one or more clinician profiles, a list of patients and patient profiles, a list of procedures to be performed on said patients, a list of clinicians scheduled to perform said procedures, other information, or combinations thereof. A clinician profile may comprise information about a clinician, including how long the clinician has worked in the medical field, the level of education attained by the clinician, the level of experience the clinician has with the medical system 10 (or similar systems), or any combination thereof.

The database 27 may be stored in the memory 24 and may be dynamically updated. Additionally or alternatively, the database 27 may be stored on a device such as a server or a portable storage device that is accessible by the control system 20 via an internal network (e.g., a secured network of a medical facility or a teleoperational system provider) or an external network (e.g. the Internet). The database 27 may be distributed throughout two or more locations. For example, the database 27 may be present on multiple devices which may include the devices of different entities and/or a cloud server. Additionally or alternatively, the database 27 may be stored on a portable user-assigned device such as a computer, a mobile device, a smart phone, a laptop, an electronic badge, a tablet, a pager, and other similar user devices.

In some embodiments, control system 20 may include one or more servo controllers that receive force and/or torque feedback from the medical instrument system 14. Responsive to the feedback, the servo controllers transmit signals to the operator input system 16. The servo controller(s) may also transmit signals instructing assembly 12 to move the medical instrument system(s) 14 and/or endoscopic imaging system 15 which extend into an internal surgical site within the patient body via openings in the body. Any suitable conventional or specialized servo controller may be used. A servo controller may be separate from, or integrated with, assembly 12. In some embodiments, the servo controller and assembly 12 are provided as part of a teleoperational arm cart positioned adjacent to the patient's body.

The control system 20 can be coupled with the endoscopic imaging system 15 and can include a processor to process captured images for subsequent display, such as to a surgeon on the surgeon's control console 17, or on another suitable display located locally and/or remotely. For example, where a stereoscopic endoscope is used, the control system 20 can process the captured images to present the surgeon with coordinated stereo images of the surgical site. Such coordination can include alignment between the opposing images and can include adjusting the stereo working distance of the stereoscopic endoscope.

In alternative embodiments, the medical system 10 may include more than one assembly 12 and/or more than one operator input system 16. The exact number of assemblies 12 will depend on the surgical procedure and the space constraints within the operating room, among other factors. The operator input systems 16 may be collocated or they may be positioned in separate locations. Multiple operator input systems 16 allow more than one operator to control one or more assemblies 12 in various combinations.

The medical system 10 may also be used to train and rehearse medical procedures. For example, the medical system 10 may be used in conjunction with the gaze-based control system described below in FIG. 2 to allow the surgeon S to communicate with other personnel in the surgical environment 11 based on the gaze of the surgeon S and to control one or more systems based on the gaze of the surgeon S.

FIG. 1B is a perspective view of one embodiment of an assembly 12 which may be referred to as a patient side cart, surgical cart, teleoperational arm cart, or surgical robot. The assembly 12 shown provides for the manipulation of three surgical tools 30a, 30b, 30c (e.g., medical instrument systems 14) and an imaging device 28 (e.g., endoscopic imaging system 15), such as a stereoscopic endoscope used for the capture of images of the site of the procedure. The imaging device may transmit signals over a cable 56 to the control system 20. Manipulation is provided by teleoperative mechanisms having a number of joints. The imaging device 28 and the surgical tools 30a-c can be positioned and manipulated through incisions in the patient so that a kinematic remote center is maintained at the incision to minimize the size of the incision. Images of the surgical site can include images of the distal ends of the surgical tools 30a-c when they are positioned within the field-of-view of the imaging device 28.

The assembly 12 includes a drivable base 58. The drivable base 58 is connected to a telescoping column 57, which allows for adjustment of the height of arms 54. The arms 54 may include a rotating joint 55 that both rotates and moves up and down. Each of the arms 54 may be connected to an orienting platform 53. The arms 54 may be labeled to facilitate trouble shooting. For example, each of the arms 54 may be emblazoned with a different number, letter, symbol, other identifier, or combinations thereof. The orienting platform 53 may be capable of 360 degrees of rotation. The assembly 12 may also include a telescoping horizontal cantilever 52 for moving the orienting platform 53 in a horizontal direction.

In the present example, each of the arms 54 connects to a manipulator arm 51. The manipulator arms 51 may connect directly to a medical instrument, e.g., one of the surgical tools 30a-c. The manipulator arms 51 may be teleoperatable. In some examples, the arms 54 connecting to the orienting platform 53 may not be teleoperatable. Rather, such arms 54 may be positioned as desired before the surgeon S begins operation with the teleoperative components. Throughout a surgical procedure, medical instruments may be removed and replaced with other instruments such that instrument to arm associations may change during the procedure.

Endoscopic imaging systems (e.g., endoscopic imaging system 15 and imaging device 28) may be provided in a variety of configurations including rigid or flexible endoscopes. Rigid endoscopes include a rigid tube housing a relay lens system for transmitting an image from a distal end to a proximal end of the endoscope. Flexible endoscopes transmit images using one or more flexible optical fibers. Digital image based endoscopes have a "chip on the tip" design in which a distal digital sensor such as a one or more charge-coupled device (CCD) or a complementary metal oxide semiconductor (CMOS) device store image data. Endoscopic imaging systems may provide two- or three-dimensional images to the viewer. Two-dimensional images may provide limited depth perception. Three-dimensional stereo endoscopic images may provide the viewer with more accurate depth perception. Stereo endoscopic instruments employ stereo cameras to capture stereo images of the patient anatomy. An endoscopic instrument may be a fully sterilizable assembly with the endoscope cable, handle and shaft all rigidly coupled and hermetically sealed.

FIG. 1C is a perspective view of an embodiment of the operator input system 16 at a surgeon's control console 17. The operator input system 16 includes a left eye display 32 and a right eye display 34 for presenting the surgeon S with a coordinated stereo view of the surgical environment that enables depth perception. The operator input system 16 further includes one or more input control devices 36, which in turn cause the assembly 12 to manipulate one or more instruments of the endoscopic imaging system 15 and/or medical instrument system 14. The input control devices 36 can provide the same degrees of freedom as their associated instruments to provide the surgeon S with telepresence, or the perception that the input control devices 36 are integral with said instruments so that the surgeon has a strong sense of directly controlling the instruments. To this end, position, force, and tactile feedback sensors (not shown) may be employed to transmit position, force, and tactile sensations from the medical instruments, e.g., surgical tools 30a-c, or imaging device 28, back to the surgeon's hands through the input control devices 36. Input control devices 37 are foot pedals that receive input from a user's foot. Aspects of the operator input system 16, the assembly 12, and the auxiliary systems 26 may be adjustable and customizable to meet the physical needs, skill level, or preferences of the surgeon S. Operator input system 16 may further include or be associated with a gaze tracking system 40 to determine a gaze point of an operator (e.g. surgeon S) with respect to a display on the left and right eye displays 32, 34. Examples of devices and methods that may be used to implement the gaze tracking system 230 are described in further detail in U.S. patent Ser. No. 15/126,074, entitled "Medical Devices, Systems, and Methods Using Eye Gaze Tracking," which is hereinafter incorporated by reference in its entirety.

Figure 2:
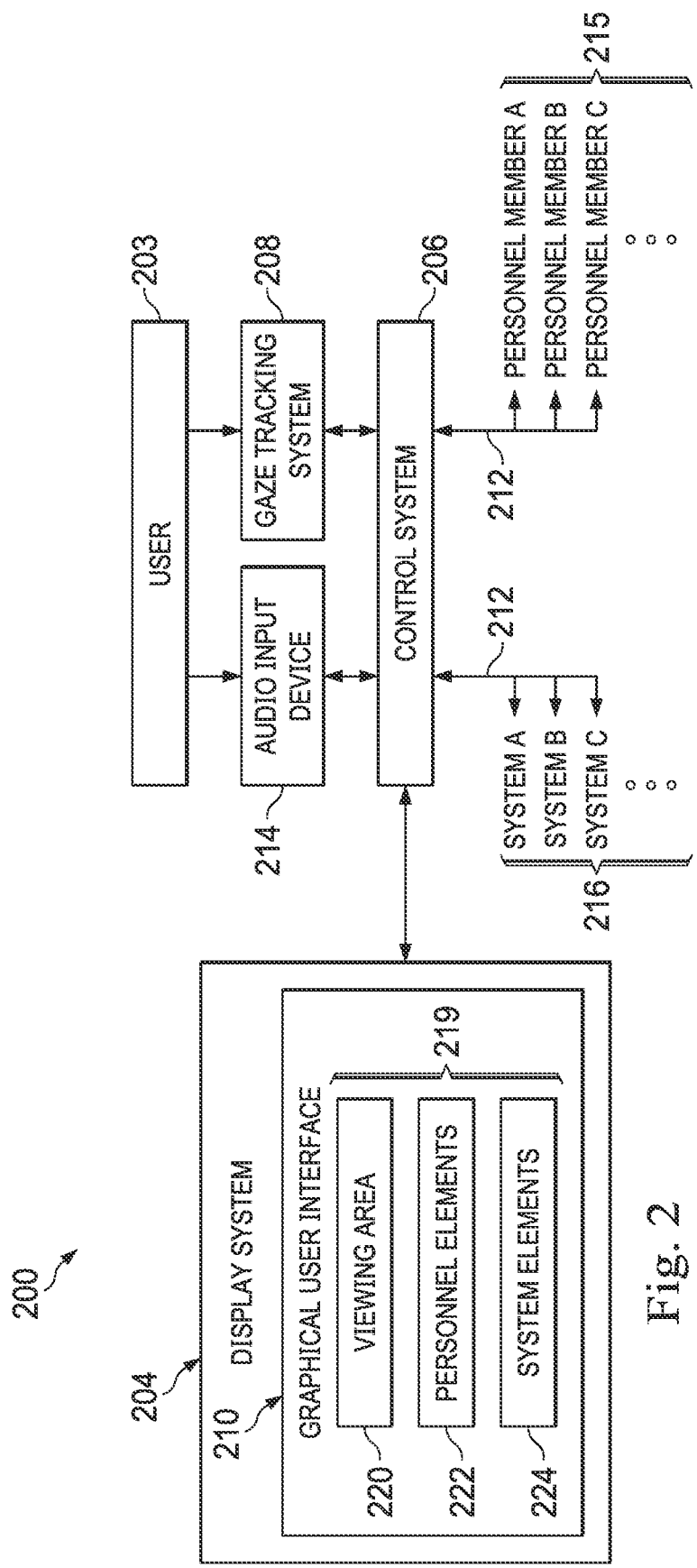
FIG. 2 is a schematic diagram of an environment in which a user may use gaze to control speech-based communications, in accordance with an embodiment.

FIG. 2 is a schematic diagram of an environment 200 in which a user 203 may use gaze to control speech-based communications. In one embodiment, the environment 200 is a medical environment, such as an operating room (e.g. the surgical environment 11 of FIG. 1A). In other embodiments, the environment 200 may be an emergency room, a surgical training environment, a medical laboratory, or some other type of environment in which any number of medical procedures or medical training procedures may take place. In some embodiments, the user 203 may be, for example, the surgeon S described in FIG. 1A. In other embodiments, the user 203 may be some other medical professional or medical operator.

The environment 200 includes a display system 204, a control system 206 (e.g., the control system 20), an audio input device 214, and a gaze tracking system 208 (e.g., the gaze tracking system 40). In one or more embodiments, the control system 206 is communicatively coupled to the display system 204 and to the gaze tracking system 208. Components may communicate with the control system through one or more wired, wireless, optical, and/or other types of communications links. In some embodiments, the gaze tracking system 208 may also be communicatively coupled to the display system 204. In one embodiment, the gaze tracking system 208 is physically coupled to the display system 204. In other embodiments, the gaze tracking system 208 may be integrated as part of the display system 204. In still other embodiments, the control system 206 is implemented as part of the display system 204.

The control system 206 may include one or more processors capable of running executable code stored on at least one memory. As one example, the control system 206 may be used to run executable code stored on memory to process information received from the gaze tracking system 208.

The display system 204 may include one or more display devices (e.g. monitors, headsets, touchscreens, etc.). In one embodiment, the display system 204 may be implemented as or as part of the surgeon's control console 17 of FIG. 1C (e.g., left and right eye displays 32, 34). The display system 204 visually presents at least one display to the user 203 that features a graphical user interface 210. The graphical user interface 210 includes a plurality of graphical elements 219 that may be controlled by a gaze input as described in detail below.

The audio input device 214 may include at least one microphone. For example, the audio input device 214 may be incorporated into the surgeon's console 17 or a headset or may be otherwise located near the user 203 in the environment 200 to allow voice communication from the user 203 to be detected and captured.

In another example embodiment, the audio input device 214 is an intercom system located within the environment 200. The intercom system may also be referred to as a multi-channel intercom system. In some embodiments, the control system 206 may be considered part of the audio input device 214. In other embodiments, one or more of the processors that make the control system 206 may be considered part of the audio input device 214.

The control system 206 may process audio information received from the audio input device 214 and selectively communicate the audio information to personnel members 215 and/or systems 216 using one or more information conveyors 212 associated with respective personnel members 215 and/or systems 216. The systems 216 may be, for example, component systems of the medical system 10. The personnel members 215 and systems 216 may be located in the environment 200 and/or may be located outside the environment.

The information conveyors 212 may include any number of communication channels, audio output devices or systems, or combination thereof for carrying, communicating, or otherwise conveying the audio information. A communication channel may include, for example, a wireless communications link, a wired communications link, a digital communication channel, an analog communication channel, an audio cable, some other type of transmission medium or logical connection, or a combination thereof. An audio output device or system may include, for example, an electroacoustic transducer (e.g. a speaker, a headset, an earbud(s), a headphone, etc.). In some embodiments, an information conveyor 212 corresponding to a system 216 may include at least one of a wire, an optical fiber, a wireless communication channel, storage media, a computer bus, or some other type of communication channel. In one or more embodiments, a communication channel or audio output device or system may be part of one of the systems 216.

The gaze tracking system 208 includes a device that tracks the eye movement (i.e. gaze) of the user 203 with respect to the graphical user interface 210 to generate gaze information that is sent to the control system 206 for processing. In some embodiments, the gaze tracking system 208 may also be referred to as an eye tracking device or eye tracking system. The gaze tracking system 208 is used to determine the direction of and/or location of the gaze of the user 203 relative to the graphical user interface 210. For example, the gaze tracking system 208 may be able to detect when the gaze of the user 203 is directed at an element 219 of the graphical user interface 210.

The graphical user interface 210 presents the elements 219 to the user 203 to allow the user 203 to selectively communicate with the personnel members 215 and/or the systems 216 through one or more information conveyors 212 based on gaze. The elements 219 may include, for example, graphical icons, display sections, windows, images, text, buttons, other types of graphical features, or a combination thereof. In some embodiments, the elements 219 may be referred to as user interface elements.

In one or more embodiments, the elements 219 include a viewing area 220, personnel elements 222, and system elements 224. The viewing area 220 may include an image(s) or a sequence of images obtained from an imaging system (e.g. the endoscopic imaging system 15 of FIG. 1A). In one embodiment, the viewing area 220 visually presents the image(s) or sequence of images to the user 203 in real-time or near real-time as a medical procedure is being performed within the environment 200. Further, the personnel elements 222 of the graphical user interface 210 may visually present to the user 203 icons that represent the personnel members 215 and their respective information conveyors 212. The system elements 224 of the graphical user interface 210 may visually present to the user 203 icons that represents the systems 216 and their respective information conveyors 212.

In some embodiments, the information conveyors 212 include audio communication channels corresponding to the personnel members 215. For example, the information conveyors 212 may include an audio communication channel for communicating audio information to each of the personnel members 215. In one embodiment, the information conveyors 212 may include an audio communication channel for communicating audio information to a team of personnel members 215. Thus, the personnel elements 222 allow the user 203 to selectively interact with the personnel members 215 over their respective information conveyors 212, which may be audio communication channels, based on the gaze of the user 203.

In particular, each personnel element 222 may identify or be associated with one or more personnel members 215 with whom the user 203 may desire or expect to communicate when the user 203 is in the environment 200. The one or more personnel members 215 may be located inside the environment 200, outside the environment 200, or both. The personnel element 222 may identify a particular person by a name, a medical profession, a medical role, a team name, a team type, a category of personnel, or some other classification for personnel. For example, the personnel element 222 may be the identification of a physician, a circulator, a first assist nurse, a scrub nurse, a sterile team, a non-sterile team, a predetermined medical team, an entire team, a technician, some other type of operator, or a combination thereof. An information conveyor 212 may include audio speakers located near a known or tracked location of the personnel member. For example, the audio speakers may be located in a headset worn by the personnel member or at a work console of the personnel member.

In some embodiments, the system elements 224 may also allow the user 203 to selectively interact with or control the systems 216 based on the gaze of the user 203. Each system element 224 may identify or be associated with one or more systems 216 to which or about which the user 203 may desire or expect to communicate when the user 203 is in the environment 200. The systems 216 may include various systems located inside the environment 200, outside the environment 200, or both. A system 216 may be, for example, without limitation, a speaker, a light device, a note-taking application, a database, a robotic device, a medical imaging device, an imaging mode, a medical system, some other type of system or group of systems, or a combination thereof.

The gaze of the user 203 may be directed at any one of the elements 219 to selectively control the use of and determine the recipient of audio information received by the audio input device 214. More specifically, gaze information generated by the gaze tracking system 208 may be processed by the control system 206 and used to control where the speech of the user 203 is focused or directed or how the speech of the user 203 is used to control other systems, such as the systems 216. Based on the gaze information, the control system 206 may change a state of the element 219 at which the gaze of the user 203 is directed. For example, each of the elements 219 may be switched between a listening state and a passive (not listening) state. The control system 206 may direct the audio information received at the audio input device 214 to the systems 216 and personnel members 215 based on the listening and passive states. The processes used to change the state of the elements 219 and control the processing of the audio information based on the gaze of the user 203 are described in greater detail below in FIGS. 4-6.

Figure 3:
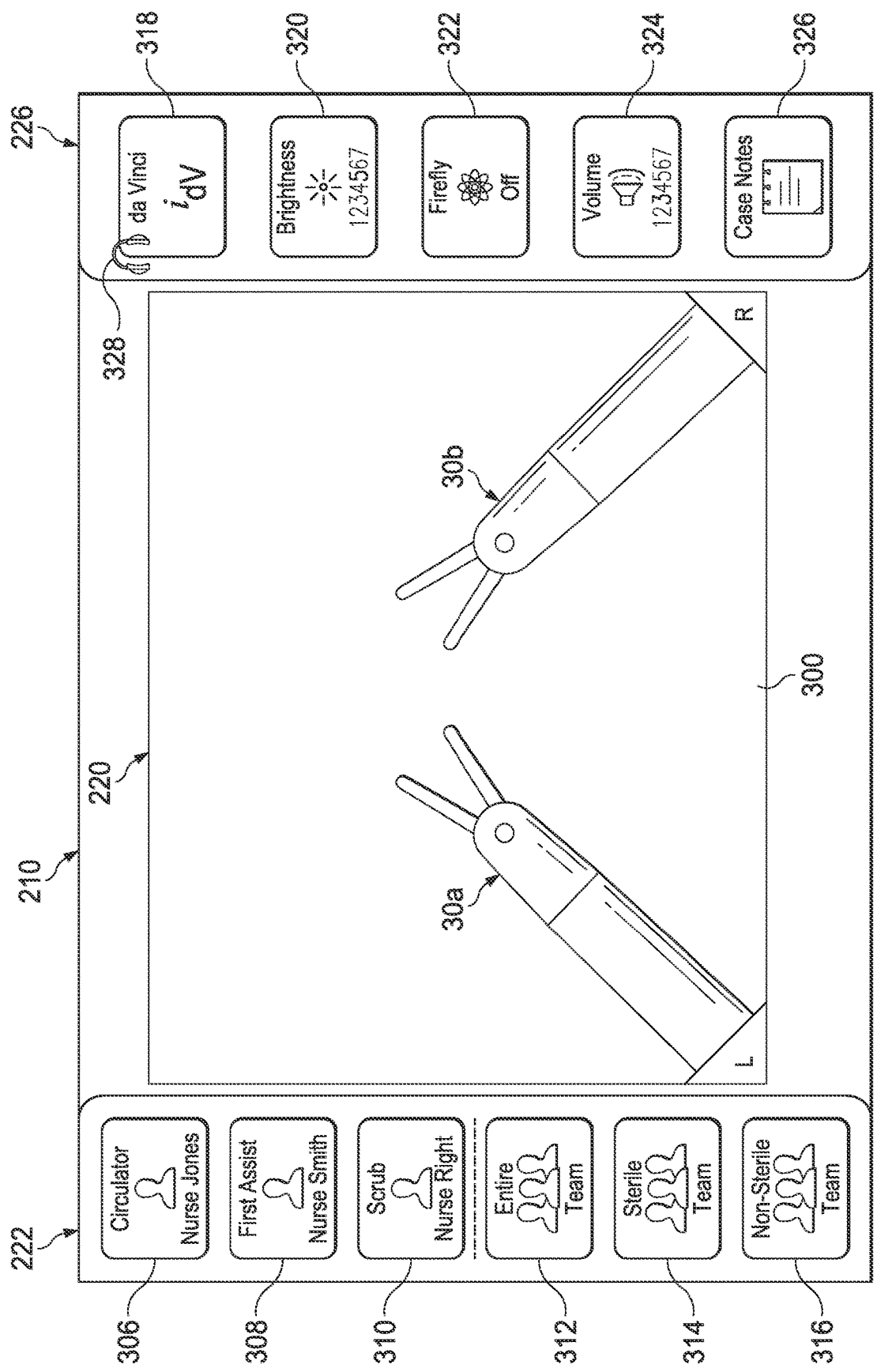
FIG. 3 is an illustration of an example embodiment of the graphical user interface from FIG. 2, in accordance with an embodiment.

FIG. 3 is an illustration of an example embodiment of the graphical user interface 210 described in FIG. 2. As depicted, the graphical user interface 210 includes the viewing area 220, the personnel elements 222, and the system elements 224.

In this example embodiment, the viewing area 220 presents an image 300 to the user 203. The image 300 is an example of one element of the plurality of elements 219 described in FIG. 2. In one embodiment, the image 300 may be obtained from, for example, the endoscopic imaging system 15 of FIG. 1A. In particular, the image 300 may be a substantially real-time image of a surgical procedure being performed by the user 203 using, for example, surgical tool and surgical tool 30b of FIG. 1B.

In one embodiment, the image 300 presented in the viewing area 220 is assigned to a default listening (e.g. activated) state for the audio input device 214 of FIG. 2 such that when a gaze of the user 203 is detected in a direction of the image 300, a state of the viewing area 220 is changed to a listening state, which thereby results in the audio input device 214 being set to the default listening state. For example, the audio input device 214 may be part of a multi-channel intercom system that includes the information conveyors 212 in the form of audio communication channels. In the default listening state, the audio input device 214 and the control system 206 may be configured such that audio input, such as the speech of user 203, is communicated across each audio communication channel. In other words, communications (i.e. the transmission of audio information) may be broadcast over all channels of the multi-channel intercom system. In some embodiments, the viewing area 220 may be set to a default listening state such that the viewing area 220 is in the default listening state, even when a gaze is not detected at the viewing area 220, until a gaze is directed at another element of the plurality of elements 219.

The personnel elements 222 include icons 306, 308, 310, 312, 314, and 316, each of which represents a different personnel member(s) 215 and is associated with a different respective information conveyor of the information conveyors 212 described in FIG. 2 for communicating audio information to the personnel member(s) 215. For example, the icons 306, 308, 310, 312, 314, and 316 represent various audio communication channels for communicating with a circulator, a first assist nurse, a scrub nurse, an entire team, a sterile team, and a non-sterile team, respectively.

The system elements 224 include icons 318, 320, 322, 324, and 326, each of which represents a different system(s) 216 and is associated with a different respective information conveyor of the information conveyors 212 for communicating audio information to the system(s) 216. For example, the icons 318, 320, 322, 324, and 326 represent component systems of the medical system 10 in FIG. 1A, including the medical system 10, an endoluminal light device, an endoluminal fluorescent device, a speaker device, and a note-taking application, respectively. In some embodiments, each of the icons 318, 320, 322, 324, and 326 may be associated with a same information conveyor 212 in the form of a communication channel, wired or wireless communications link, storage media, or computer bus specifically dedicated to receiving voice commands for the systems 216 represented by these icons.

In one or more embodiments, a graphical feature 328 may be displayed in association with any of the icons 306-326 to present additional information to the user 203 about the listening or passive state of an element and the respective information conveyor 212. For example, the graphical feature 328 may be used to indicate when the particular one of the icons 306-326 is set to a listening state. A listening state for a particular icon indicates that audio information received at the audio input device 214 will be communicated through the information conveyor 212 associated with the particular icon to the personnel member(s) and/or system(s) represented by the particular icon. In other words, the listening state for a particular icon indicates that the information conveyor 212 associated with the particular icon will be "listening" for audio (e.g. speech) input.

In this example embodiment, the graphical feature 328 is displayed in association with the icon 318. The graphical feature 328 is a visual cue indicating to the user 203 that any speech of the user 203 will be directed at the medical system 10 of FIG. 1A represented by the icon 318. In various embodiments, multiple graphical features 328 may appear in the graphical user interface 210. For example, if the user 203 gazes at the icons 306 and 308, the graphical features may appear next to icons 306 and 308, indicating that audio information received at the audio input device 214 will be directed to the information conveyors 212 associated with personnel members Circulator Nurse Jones and First Assistant Nurse Smith. The graphical feature 328, which may also be referred to as a graphical cue, may be a graphical depiction of a set of headphones as shown. Alternatively, the graphical feature 328 may be another symbol, a color change of the element, an outline of the element, or any other visual cue to distinguish listening, or gaze-selected, elements from passive, or unselected, elements.

In some example embodiments, textual cues may be displayed in association with an icon. These textual cues may indicate to the user 203 the particular voice commands that may be used to control the particular system represented by a corresponding icon. For example, the textual cue "ON" and the textual cue "OFF" may be displayed over or near the icon 322. These textual cues may indicate to the user 203 that the voice commands of "ON" or "OFF" can be used to control the system represented by the icon 322. As another example, the textual cues "BRIGHTER" and "DIMMER" may be displayed over or near the icon 320 to indicate the voice commands that can be used to control the system represented by the icon 320. In this manner, textual cues may be used to "seed" the user 203 with verbiage for the voice commands that are supported by speech recognition and that may be used to control different systems. Further, the textual cues may also provide a mechanism to improve the usability and reliability of speech recognition by suggesting terms or phrases that are optimized based on various criteria. For example, the textual cues may be selected such that they are short, phonetically distinct, easy to enunciate, easy to remember, optimized in some other manner, or a combination thereof.

Figure 4:
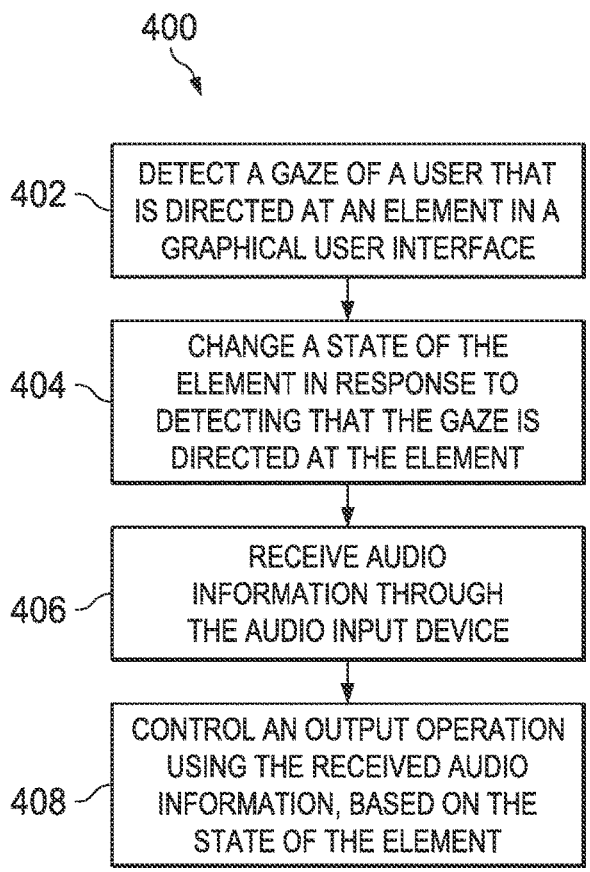
FIG. 4 is a flowchart illustration of a method for performing gaze-based communications, in accordance with an embodiment.

FIG. 4 is a flowchart illustration of a method 400 for performing gaze-based communications. In one or more embodiments, the gaze-based communications are to be performed in the environment 200 of FIG. 2 (e.g. the surgical environment 11 of FIG. 1A). The method 400 is illustrated in FIG. 4 as a set of operations or processes 402 through 408 and is described with continuing reference to FIGS. 2-3. Not all of the illustrated processes 402 through 408 may be performed in all embodiments of method 400. Additionally, one or more processes that are not expressly illustrated in FIG. 4 may be included before, after, in between, or as part of the processes 402 through 408. In some embodiments, one or more of the processes 402 through 408 may be implemented, at least in part, in the form of executable code stored on non-transitory, tangible, machine-readable media that when run by one or more processors (e.g., the processors of control system) may cause the one or more processors to perform one or more of the processes.

At process 402, a gaze of the user 203 is detected being directed at an element 219 in the graphical user interface 210. At process 404, a state of the element 219 is changed in response to detecting that the gaze is directed at the element 219. For example, the element 219 may be switched from a passive state (or not listening state) to a listening state.

When the element 219 represents one or more personnel members 215, the listening state indicates that speech received through the audio input device 214 will be directed to at least one corresponding information conveyor 212 associated with the element 219 and that enables the speech to be communicated to the one or more personnel members 215. When the element 219 represents one or more systems 216, the listening state indicates that speech received through the audio input device 214 will be directed to at least one corresponding information conveyor 212 associated with the element 219 dedicated to receiving voice commands for the one or more systems 216. The speech (e.g. voice commands) may then be processed using speech recognition context information designated for that system to generate output information that may then be used to control the operation of the one or more systems 216. In some embodiments, activating the state of any element may include activating the audio input device 214.

At process 406, audio information is then received through the audio input device 214. At process 408, an output operation of the control system 206 is controlled based on the state of the element 219 such that audio information received through the audio input device 214 is directed to at least one information conveyor 212 associated with the element 219. The audio information may include, for example, without limitation, a voice command, audio instructions, an audio report, audio commentary related to a surgical procedure, some other type of verbal communication, or a combination thereof. In some embodiments, the audio information may be the oral dictation of a surgical case note by the user 203, which, in some cases, may be recorded by the audio input device 214 at process 406.

With respect to process 408, the control system 206 may control the output operation in different ways. For example, based on the state of the viewing area 220, the control system 206 may control whether or not the audio input device 214 is in a passive state. More specifically, the control system 206 may control whether the audio input device 214 is listening or not listening (passive). In another example, based on the state of the personnel element 222 representing a selected personnel member 215, the control system 206 controls the output operation to determine whether to direct an audio output signal to an information conveyor 212 in the form of a communication channel associated with the selected personnel member 215. If the state of the personnel element 222 is listening, the audio output signal is transmitted via the communication channel. If the state of the personnel element 222 is passive, the audio output signal is not transmitted via the communication channel. The control system 206 ensures that all communication channels associated with elements at which a gaze was not detected, and which thus remain in a passive state, receive no output communication.

In yet another example, based on the state of the system element 224 representing a system 216, the control system 206 controls the output operation to determine whether to direct audio input received through the audio input device 214 to a dedicated communication channel for voice commands for the system 216. If the state of the system element 224 is listening, the control system 206 may direct the audio input to the dedicated communication channel for voice commands for the system 216 represented by the system 216 and may then process the audio input received from the audio input device 214 using the speech recognition context information designated for the system element 224. This processing may generate output information that may then be used to control operation of the represented system 216. In this manner, the control system 206 uses the gaze of the user 203 to determine to which of the information conveyors 212 the audio information of the user 203 should be directed.

In still other embodiments, the graphical user interface 210 may present a real-time image of the environment 200 and the element 219 may be a headset worn by a person in the real-time image. Controlling the output operation at process 408 may include, for example, identifying the information conveyor 212 dedicated to at least one of the headset or the person wearing the headset and directing the audio information to the identified information conveyor 212.

Figure 5:
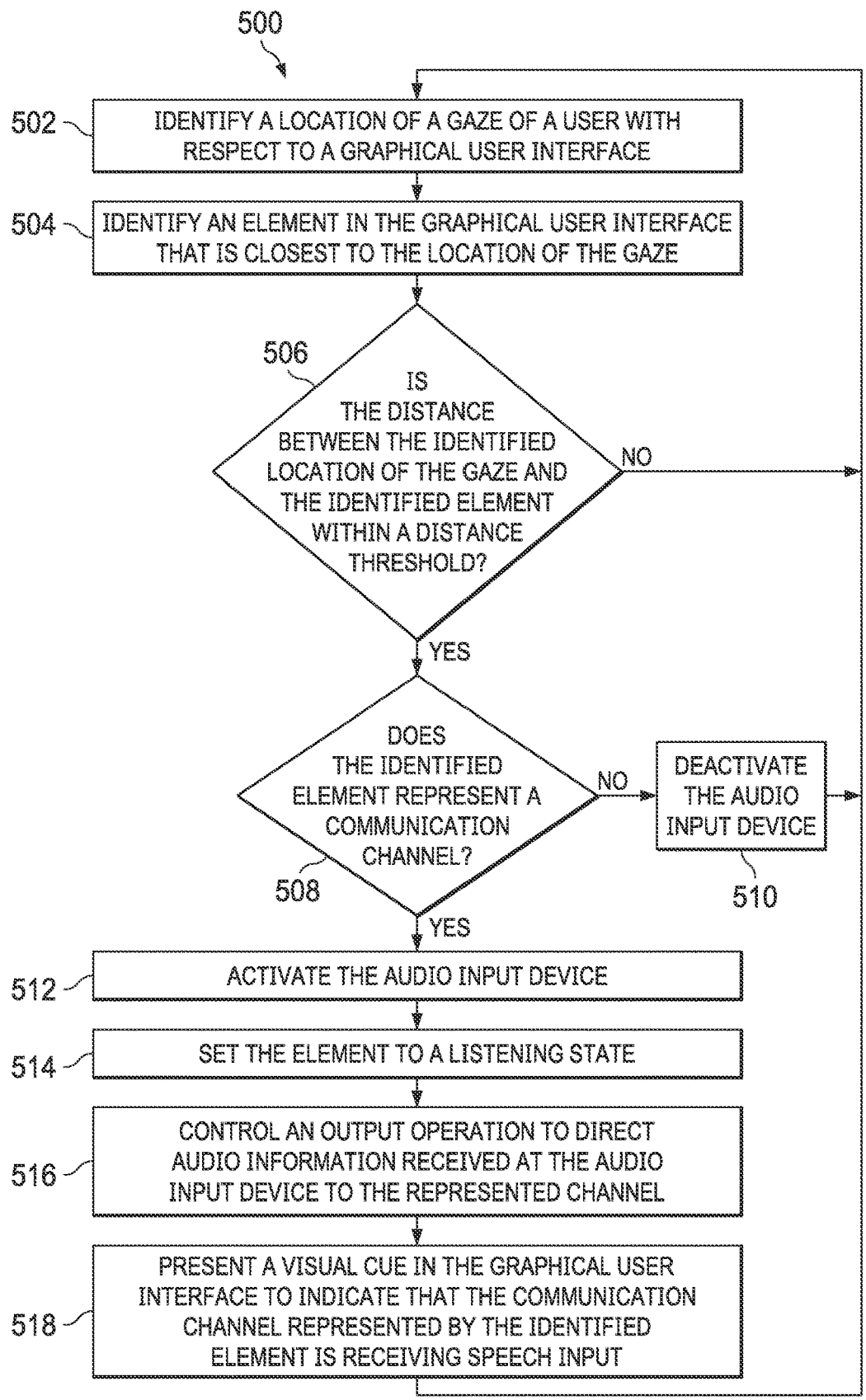
FIG. 5 is a flowchart illustration of a method for selectively controlling communications over audio communication channels based on gaze, in accordance with an embodiment.

FIG. 5 is a flowchart illustration of a method 500 for selectively controlling communications over communication channels based on gaze. In one or more embodiments, the gaze-based communications are to be performed in the environment 200 of FIG. 2 (e.g. the surgical environment 11 of FIG. 1A). The method 500 is illustrated in FIG. 5 as a set of operations or processes 502 through 518 and is described with continuing reference to FIGS. 2-3. Not all of the illustrated processes 502 through 518 may be performed in all embodiments of method 500. Additionally, one or more processes that are not expressly illustrated in FIG. 5 may be included before, after, in between, or as part of the processes 502 through 518. In some embodiments, one or more of the processes 502 through 518 may be implemented, at least in part, in the form of executable code stored on non-transitory, tangible, machine-readable media that when run by one or more processors (e.g., the processors of control system) may cause the one or more processors to perform one or more of the processes.

At process 502, a location of the gaze of the user 203 with respect to the graphical user interface 210 is identified. In one embodiment, the location of the gaze is identified based on the direction of the gaze of the user 203. In one or more embodiments, the location of the gaze is identified as a location in the graphical user interface 210 with respect to the coordinate system of the graphical user interface 210. At process 504, the element 219 in the graphical user interface 210 that is closest to the location of the gaze is identified.

At process 506, a determination is made as to whether the distance between the identified location of the gaze and the identified element 219 is within a distance threshold. In some embodiments, the distance threshold may be about one to five centimeters. In other embodiments, the distance threshold may be between about two and ten millimeters. If the element 219 in the graphical user interface 210 identified as closest to the location of the gaze is not within the distance threshold, the method 500 returns to process 502. Otherwise, at process 508, a determination is made as to whether the identified element 219 is associated with a communication channel (e.g. audio communication channel). The communication channel may allow the communication of audio information (e.g. audio output) to one or more personnel members 215.

If the identified element 219 does not represent a communication channel, at process 510, the audio input device 214 may, optionally, be deactivated (e.g. set to the passive state), with the method 500 then returning to process 502 as described above. Otherwise, at process 512, the audio input device 214 may be activated (e.g. set to the listening state) to enable the audio input device 214 to receive audio input. In some embodiments, the audio input device 214 may be considered activated or listening even if no communication channels are selected. In this case, audio information may be received, recorded, or processed for other purposes that output to a communication channel.

At process 514, the element identified by the user's gaze is set to a listening state. At process 516, an output operation of the control system 206 is controlled based upon the listening state of the identified element 219 to direct audio information received at the audio input device 214 to the associated communication channel. For example, the audio information received through the audio input device 214 is directed to the communication channel that corresponds to the one or more personnel members represented by the identified element 219. For example, when the audio input device 214 is part of a multi-channel intercom system, the topology of the multi-channel intercom system may be adjusted to selectively direct speech input to the communication channel of the multi-channel intercom system that is associated with or represented by the identified element 219.

Optionally, at process 518, a visual cue may be presented in the graphical user interface 210 to indicate that speech input is being directed to the communication channel represented by the identified element 219. Optionally, in some embodiments, after the state of the identified element 219 has been set to the listening state, a visual alert may be generated on a different display device in the environment 200. This visual alert may be used to alert the one or more personnel members represented by the identified element 219 that speech input will be directed their way. In one example embodiment, the visual alert may be the illumination of a light emitting diode on the headset of a nurse in the environment 200. In some cases, an audio alert may be generated through an electroacoustic transducer in the environment 200 in addition to or instead of the visual alert. The audio alert may be, for example, a computer-generated verbal cue, a chime, a ring, or some other type of audible tone.

Figure 6:
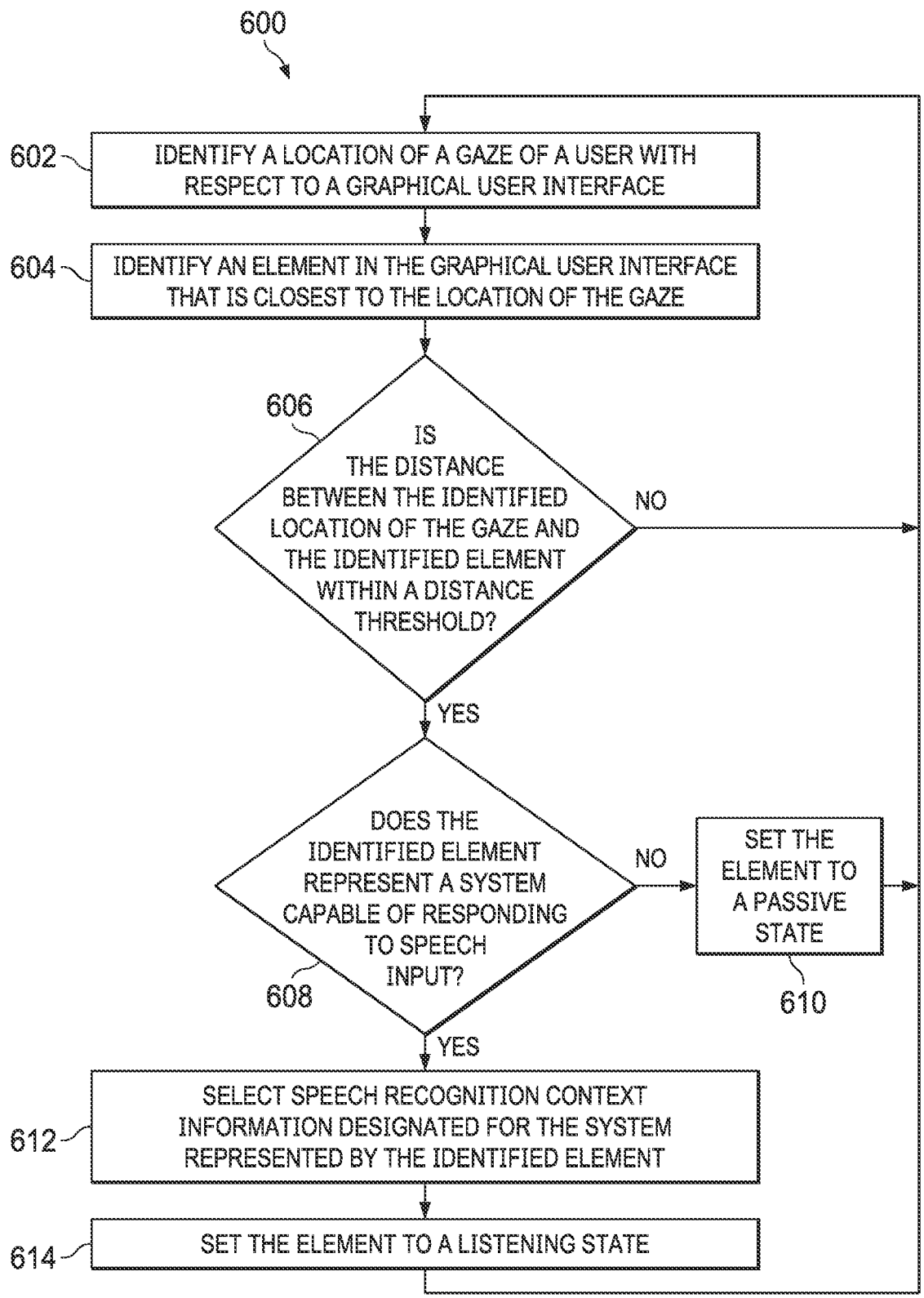
FIG. 6 is a flowchart illustration of a method for selectively controlling the operation of systems based on gaze, in accordance with an embodiment.

FIG. 6 is a flowchart illustration of a method 600 for selectively controlling the operation of systems 216 based on gaze. In one or more embodiments, the gaze-based communications are to be performed in the environment 200 of FIG. 2 (e.g. the surgical environment 11 of FIG. 1A). The method 600 is illustrated in FIG. 6 as a set of operations or processes 602 through 614 and is described with continuing reference to FIGS. 2-3. Not all of the illustrated processes 602 through 614 may be performed in all embodiments of method 600. Additionally, one or more processes that are not expressly illustrated in FIG. 6 may be included before, after, in between, or as part of the processes 602 through 614. In some embodiments, one or more of the processes 602 through 614 may be implemented, at least in part, in the form of executable code stored on non-transitory, tangible, machine-readable media that when run by one or more processors (e.g., the processors of control system) may cause the one or more processors to perform one or more of the processes.

At process 602, a location of the gaze of the user 203 with respect to the graphical user interface 210 is identified. In one embodiment, the location of the gaze is identified based on the direction of the gaze of the user 203. In one or more embodiments, the location of the gaze is identified as a location in the graphical user interface 210 with respect to the coordinate system of the graphical user interface 210. At process 604, the element 219 in the graphical user interface 210 that is closest to the location of the gaze is identified.

At process 606, a determination is made as to whether the distance between the identified location of the gaze and the identified element 219 is within a distance threshold. In some embodiments, the distance threshold may be about one to five centimeters. In other embodiments, the distance threshold may be between about two and ten millimeters. If the element 219 in the graphical user interface 210 identified as closest to the location of the gaze is not within the distance threshold, the method 600 returns to process 602. Otherwise, at process 608, a determination is made as to whether the identified element 219 represents a system 216 that is responsive to speech input (i.e. voice input).

If the identified element 219 does not represent a system 216 that is responsive to speech input, then at process 610, the identified element 219 is set to a passive state. Setting the identified element 219 to a passive state may include, for example, presenting a visual cue that indicates the identified element 219 is in the passive state. For example, the visual appearance of the identified element 219 may be changed to indicate that the identified element 219 is in the passive state. The visual appearance of the element 219 may be changed by, for example, highlighting the element 219, bolding text associated with the element 219, displaying a border around the element 219, changing a color of the element 219, displaying a line across the element 219, changing a size of the element 219, or modifying the appearance of the element 219 in some other manner. The method 600 then returns to process 602 as described above.

With reference again to process 608, if the identified element 219 represents a system 216 that is responsive to speech input, then at process 612, speech recognition context information designated for the system 216 represented by the identified element 219 is selected. The speech recognition context information may be obtained from, for example, without limitation, a database storing speech recognition context information corresponding to various systems. In one example embodiment, the speech recognition context information includes information about what voice commands are valid for a particular system.

For example, the identified element 219 may be an icon that represents an instrument. In particular, the identified element 219 may be an icon representing an ejection mode for the instrument. Speech recognition context information for this instrument may identify that the word "EJECT" is a valid voice command for the instrument only when the gaze of the user 203 is directed at this particular icon.

As another example embodiment, when the identified element 219 represents a medical imaging system, the speech recognition context information for the medical imaging system may identify voice commands that are only valid for the medical imaging system. In some cases, the speech recognition context information for the medical imaging system may distinguish between an inactive mode and an active mode for the medical imaging system. For example, when the medical imaging system is in the inactive mode, the speech recognition context information may identify "ON," "TURN ON," "ENABLE," and "ACTIVATE" as the only valid voice commands for the medical imaging system. But when the medical imaging system is in the active mode, the speech recognition context information may identify "OFF," "TURN OFF," "DISABLE," and "DEACTIVATE" as the only valid voice commands for the medical imaging system.

At process 614, the identified element 219 is set to a listening state. Setting the identified element 219 to a listening state may include presenting a visual cue indicating that the element 219 is in the listening state. For example, a graphical feature may be displayed over the identified element 219. In other examples, the visual appearance of the element 219 may be changed in any manner that distinguishes the listening state from the passive state. For example, the visual appearance of the element 219 may be changed by highlighting the element 219, bolding text associated with the element 219, displaying a border around the element 219, changing a color of the element 219, changing a size of the element 219, or modifying the appearance of the element 219 in some other manner. The method 600 may then return to process 602 as described above.

In some embodiments, the process 614 also includes controlling an output operation to direct audio information received through the audio input device 214 to the information conveyor 212 associated with the identified element 219 to thereby control operation of the represented system 216. For example, at process 614, activating the element 219 may change the configuration of the audio input device 214 such that all audio input is directed to an information conveyor 212, such as a communication channel, designated for receiving voice commands for the represented system. Further, in some examples, activating the element 219 may configure the audio input device 214 such that no audio input is transmitted on any other information conveyors other than the communication channel designated for receiving voice commands for the represented system 216.

In some embodiments, directing the audio information to the information conveyor 212 associated with the identified element 219 includes directly communicating the audio information to the system 216 over a wired or wireless communications link. In other embodiments, directing the audio information to the information conveyor 212 associated with the identified element 219 includes sending the audio information via a computer bus, a wired or wireless communications link, or storage media for processing by the control system 206 to generate output information that may then be sent to the represented system 216. In still other embodiments, directing the audio information to the information conveyor 212 associated with the identified element 219 includes first processing the audio information using speech recognition context information selected based on the identified element 219 to generate output information and then sending the output information to the system 216 represented by the identified element 219 over the information conveyor 212 associated with the identified element 219.

In some examples, the audio input device 214 may be listening when the element 219 is set to the listening state. In other examples, multiple information conveyors 212 (e.g. communication channels) may be passive (or not listening) and a single communication channel dedicated for receiving voice commands for the system may be listening.

Figure 7:
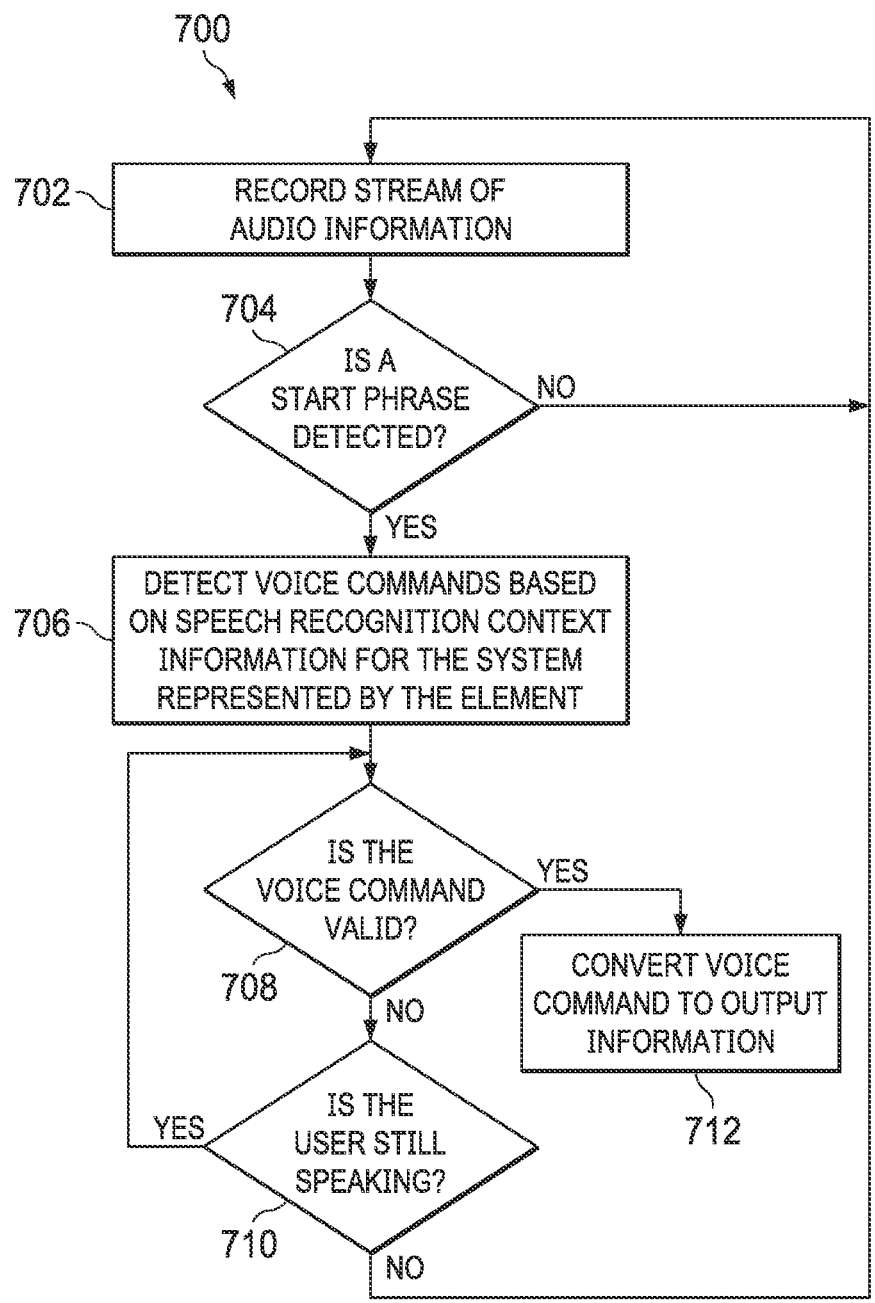
FIG. 7 is a flowchart illustration of a method for processing voice commands after an element has been set to a listening state, in accordance with an embodiment.

FIG. 7 is a flowchart illustration of a method 700 for processing voice commands after an element has been set to a listening state. In one or more embodiments, the gaze-based communications are to be performed in the environment 200 of FIG. 2 (e.g. the surgical environment 11 of FIG. 1A). The method 700 may be used to process voice commands after the element 219 is set to the listening state in process 614 of method 600. The method 700 is illustrated in FIG. 7 as a set of operations or processes 702 through 708 and is described with continuing reference to FIGS. 2-3. Not all of the illustrated processes 702 through 708 may be performed in all embodiments of method 700. Additionally, one or more processes that are not expressly illustrated in FIG. 7 may be included before, after, in between, or as part of the processes 702 through 708. In some embodiments, one or more of the processes 702 through 708 may be implemented, at least in part, in the form of executable code stored on non-transitory, tangible, machine-readable media that when run by one or more processors (e.g., the processors of control system) may cause the one or more processors to perform one or more of the processes.

At process 702, a stream of audio information begins recording. At process 704, a determination is made as to whether a start phrase has been detected. If no start phrase has been detected, the method 700 returns to process 702 described above. Otherwise, at process 706, the method 700 waits until a voice command is detected based on the speech recognition context information for the system represented by the element 219. At process 708, a determination is made as to whether the voice command is valid. If the voice command is valid, then at process 710, the voice command is converted to output information (e.g. a system command) for the system represented by the element 219. This system command may be sent to the system itself, a manager, a supervisor, or some other person.

With reference again to process 708, if the voice command is not valid, a determination is made as to whether the user 203 is still speaking. If the user is not still speaking, the method 700 returns to process 702 described above. Otherwise, the method 700 returns to process 706 described above. In this manner, once an element 219 representing a system has been set to a listening state, the control system 206 will repeatedly attempt to identify a valid voice command from the audio stream. The looped method 700 illustrated in FIG. 7 may be terminated or ended once the element 219 is identified as no longer being in the listening state.

The method 600 described in FIG. 6 and the method 700 described in FIG. 7 involve processes that may improve the efficiency with which systems 216 are controlled in the environment 200. For example, the user 203 may be able to use abbreviated voice commands that the control system 206 will convert into system commands. By using gaze to initiate the speech recognition (e.g. voice command recognition) process, the user 203 may not need to leave, for example, the surgeon's control console 17 of FIG. 1A or worry about pressing buttons with his or her hands while he or she is in the middle of performing or training for a surgical procedure. By using gaze-initiated selection of speech recognition context information designated for a particular system 216 prior to giving the voice command for a system 216, the processing resources and time need to recognize and process voice commands may be greatly reduced.

Figure 8:
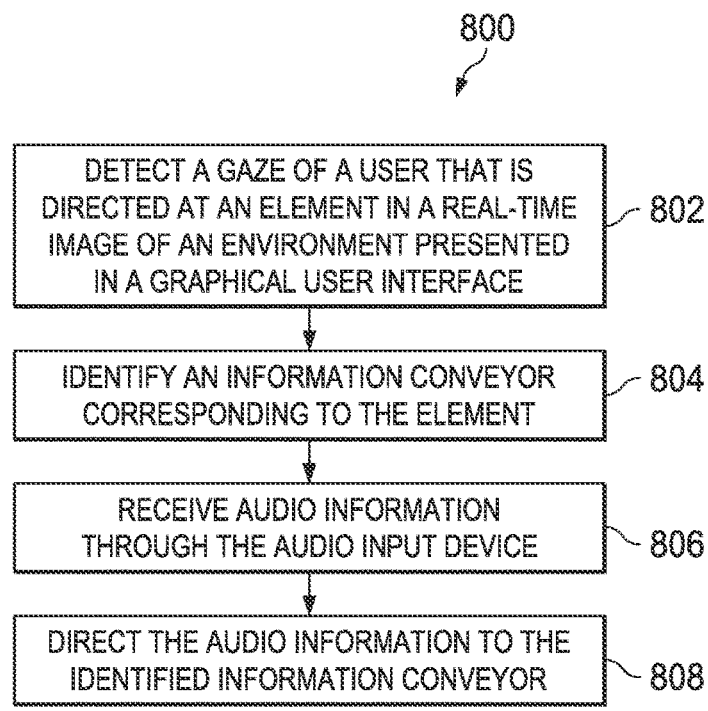
FIG. 8 is a flowchart illustration of a method for conveying audio information to a particular information conveyor assigned to a particular headset, in accordance with an embodiment.

FIG. 8 is a flowchart illustration of a method 800 for conveying audio information to a particular information conveyor assigned to a particular headset using gaze. In one or more embodiments, the gaze-based communications are to be performed in the environment 200 of FIG. 2 (e.g. the surgical environment 11 of FIG. 1A). The method 800 is illustrated in FIG. 8 as a set of operations or processes 802 through 808 and is described with continuing reference to FIG. 2. Not all of the illustrated processes 802 through 808 may be performed in all embodiments of method 800. Additionally, one or more processes that are not expressly illustrated in FIG. 8 may be included before, after, in between, or as part of the processes 802 through 808. In some embodiments, one or more of the processes 802 through 808 may be implemented, at least in part, in the form of executable code stored on non-transitory, tangible, machine-readable media that when run by one or more processors (e.g., the processors of control system) may cause the one or more processors to perform one or more of the processes.

At process 802, a gaze is detected in which the gaze is of the user 203 that is directed at an element 219 in a real-time image of an environment 200 presented in the graphical user interface 210 displayed on the display system 204 located in the environment 200. In one or more embodiments, the real-time image may be a live video of a medical environment (e.g. surgical environment 11 in FIG. 1A). In some embodiments, the real-time image may be generated by an imaging device worn by or otherwise attached to the user 203. The imaging device may have, for example, a wide field of view. In some cases, the imaging device may have a 360-degree field of view. In one or more embodiments, the element 219 is a headset that is worn by a person in the environment 200. The person may be a personnel member 215 such as, for example, a member of an operating staff, a clinician, a nurse, or some other type of person.

In some embodiments, the detection of the gaze being directed at the element 219 at process 802 may result in a state of the element 219 changing to a listening state. For example, the graphical user interface 210 may display a visual indicator to indicate that the gaze has been detected directed at the element 219. The visual indicator may be a text indicator, a graphical indicator displayed over the element 219, or some other type of visual indicator.

At process 804, an information conveyor 212 corresponding to the element 219 is identified. Process 804 may be performed in different ways. In some embodiments, a coded light pattern corresponding to the headset is identified. The coded light pattern may be presented in the environment 200 using a light device. The light device may be, for example, a light emitting diode (LED) or LED system. The coded light pattern may then be detected using an imaging device. This imaging device may have, for example, a high frame-rate to capture the coded light pattern. The information conveyor 212 dedicated to at least one of the headset or the person wearing the headset may then be identified in response to the detected coded light pattern.

In other embodiments, a fiducial marker corresponding to the headset in the real-time image may be detected in response to the gaze being directed at the headset. The fiducial marker may be, for example, a tape marker, an infrared-reflective marker, a fiducial pattern, or some other type of fiducial marker. The information conveyor 212 dedicated to at least one of the headset or the person wearing the headset may be identified based on the detected fiducial marker.

The information conveyor 212 identified at process 804 may be designated either for the specific person wearing the headset or a particular role or responsibility. For example, a particular headset may only be worn by scrub nurses. In this manner, the association between a particular headset and a particular person or role, and thereby the corresponding information conveyor 212, may be predefined.

In other embodiments, identifying the information conveyor 212 at process 804 may include verifying that the information conveyor 212 should be used for directing audio information to the person wearing the headset. For example, machine learning or adaptive learning methods may be used to identify the person wearing a headset. In one embodiment, a headset may be configured to process speech from a microphone associated with the headset to thereby identify the person wearing the headset based on speech patterns. The information conveyor 212 may only be identifiable or selectable at process 804 when the person wearing the headset has been authorized or validated.

At process 806, audio information is received through the audio input device 214. The audio input device 214 may have been activated either by the gaze being directed at the element 219, the state of the element 219 changing to the listening state, or the identification of the information conveyor 212. At process 808, the audio information is directed to the identified information conveyor 212.

The method 800 may allow the user 203 (e.g. surgeon S) to virtually look around the environment 200, observe the personnel members 215 in the environment 200, and then selectively communicate with a particular person by simply gazing at the headset worn by the person. In some embodiments, the headset may use a sensor, switch, or other control to determine when the headset is worn by a person, when the headset is worn by an authorized person, or both. Accordingly, audio information may only be directed to the information conveyor 212 identified as dedicated to the headset when the headset is actually being worn by a person or when the headset is actually being worn by an authorized person.

Thus, the embodiments described above provide a method and apparatus for enabling gaze-based communications. Gaze tracking within the environment (e.g. in conjunction with the surgeon's control console 17 of FIG. 1A) may provide a natural and easy way for the user 203 to selectively engage in conversations with individuals or groups of persons over a multi-channel intercom system. Further, gaze tracking may provide a natural and easy way for voice commands to be selectively directed towards systems in the presence of multiple systems in the environment 200.

One or more elements in embodiments of the invention may be implemented in software to execute on a processor of a computer system such as control processing system. When implemented in software, the elements of the embodiments of the invention are essentially the code segments to perform the necessary tasks. The program or code segments can be stored in a processor readable storage medium or device that may have been downloaded by way of a computer data signal embodied in a carrier wave over a transmission medium or a communication link. The processor readable storage device may include any medium that can store information including an optical medium, semiconductor medium, and magnetic medium. Processor readable storage device examples include an electronic circuit; a semiconductor device, a semiconductor memory device, a read only memory (ROM), a flash memory, an erasable programmable read only memory (EPROM); a floppy diskette, a CD-ROM, an optical disk, a hard disk, or other storage device. The code segments may be downloaded via computer networks such as the Internet, Intranet, etc.

Note that the processes and displays presented may not inherently be related to any particular computer or other apparatus. Various general-purpose systems may be used with programs in accordance with the teachings herein, or it may prove convenient to construct a more specialized apparatus to perform the operations described. The required structure for a variety of these systems will appear as elements in the claims. In addition, the embodiments of the invention are not described with reference to any particular programming language. It will be appreciated that a variety of programming languages may be used to implement the teachings of the invention as described herein.

While certain exemplary embodiments of the invention have been described and shown in the accompanying drawings, it is to be understood that such embodiments are merely illustrative of and not restrictive on the broad invention, and that the embodiments of the invention not be limited to the specific constructions and arrangements shown and described, since various other modifications may occur to those ordinarily skilled in the art.

What is claimed is:

1. A system comprising:
   a display configured to present a graphical user interface including a viewing area and one or more user interface elements;
   a gaze tracking device configured to detect a change in a gaze of a user while the user views the graphical user interface presented on the display;
   an audio input device configured to receive audio information; and
   one or more processors configured to:
      process the audio information received at the audio input device in accordance with a first mode to direct the received audio information as audio output to one or more audio output devices; and
      in response to the gaze tracking device detecting the change in the gaze of the user, process the received audio information in accordance with a second mode, the second mode being distinct from the first mode, wherein detecting the change in the gaze of the user is detecting that the gaze of the user has shifted away from the viewing area and is directed at one of the one or more user interface elements.

2. The system of claim 1, wherein detecting the change in the gaze of the user comprises detecting that the gaze of the user is directed away from the viewing area.

3. The system of claim 1, wherein:
   the one or more audio output devices comprise a plurality of audio output devices for a plurality of personnel;
   processing the audio information received at the audio input device in accordance with the first mode comprises directing the received audio information as audio output to each of the plurality of audio output devices of the plurality of personnel; and
   processing the audio information received at the audio input device in accordance with the second mode comprises directing the audio information as audio output to a subset of the plurality of audio output devices, the subset of the plurality of audio output devices being associated with a subset of the plurality of personnel.

4. The system of claim 3, wherein detecting the change in the gaze of the user comprises detecting that the gaze of the user is directed to a first user interface element of the one or more user interface elements, the first user interface element being associated with the subset of the plurality of personnel.

5. The system of claim 1, wherein processing the audio information received at the audio input device in accordance with the second mode comprises processing the audio information as one or more voice commands for the system.

6. The system of claim 5, wherein detecting the change in the gaze of the user comprises detecting that the gaze of the user is directed to a first user interface element of the one or more user interface elements, the first user interface element being associated with activating voice commands for the system.

7. The system of claim 1, wherein the one or more processors are further configured to:
   in response to the gaze tracking device detecting the change in the gaze of the user, cause the display to present a visual indication that the received audio information is being processed in accordance with the second mode.

8. The system of claim 1, wherein the one or more processors are further configured to:
   in response to the gaze tracking device detecting the gaze of the user being directed at a first user interface element of the one or more user interface elements, modify an appearance of the first user interface element.

9. The system of claim 1, wherein the system is a teleoperated surgical system; and
   wherein the one or more processors are further configured to cause the display to present an image of a surgical site within the viewing area.

10. The system of claim 1, wherein the display is a stereo viewer.

11. A method comprising:
    presenting, on a display, a graphical user interface including a viewing area and one or more user interface elements;
    detecting, by a gaze tracking device, a change in the gaze of a user while the user views the graphical user interface presented on the display;
    receiving, by an audio input device, audio information;
    processing the audio information received at the audio input device in accordance with a first mode to direct the received audio information as audio output to one or more audio output devices; and in response to the gaze tracking device detecting the change in the gaze of the user, processing the received audio information in accordance with a second mode, the second mode being distinct from the first mode, wherein detecting the change in the gaze of the user is detecting that the gaze of the user has shifted away from the viewing area and is directed at one of the one or more user interface elements.

12. The method of claim 11, wherein detecting the change in the gaze of the user comprises detecting that the gaze of the user is directed away from the viewing area.

13. The method of claim 11, wherein the one or more audio output devices comprise a plurality of audio output devices for a plurality of personnel;

wherein processing the audio information received at the audio input device in accordance with the first mode comprises directing the received audio information as audio output to each of the plurality of audio output devices of the plurality of personnel; and wherein processing the audio information received at the audio input device in accordance with the second mode comprises directing the audio information as audio output to a subset of the plurality of personnel.

14. The method of claim 13, wherein detecting the change in the gaze of the user comprises detecting that the gaze of the user is directed to a first user interface element of the one or more user interface elements, the first user interface element being associated with the subset of the plurality of personnel.

15. The method of claim 11, wherein processing the audio information received at the audio input device in accordance with the second mode comprises processing the audio information as one or more voice commands.

16. The method of claim 15, wherein detecting the change in the gaze of the user comprises detecting that the gaze of the user is directed to a first user interface element of the one or more user interface elements, the first user interface element being associated with activating voice commands.

17. The method of claim 11, further comprising:

in response to detecting the change in the gaze of the user, presenting a visual indication that the received audio information is being processed in accordance with the second mode.

18. The method of claim 11, further comprising:

in response to detecting the change the gaze of the user being directed to a first user interface element, modifying an appearance of the first user interface element.

19. The method of claim 11, further comprising:

presenting an image of a surgical site within the viewing area.

20. A non-transitory computer-readable medium storing instructions that, when executed by one or more processors of a system, cause the system to:

present, on a display, a graphical user interface including a viewing area and one or more user interface elements;

detect, by a gaze tracking device, a change in a gaze of a user while the user views the graphical user interface presented on the display;

receive, by an audio input device, audio information;

process the audio information received at the audio input device in accordance with a first mode to direct the received audio information as audio output to one or more audio output devices; and in response to the gaze tracking device detecting the change in the gaze of the user, processing the received audio information in accordance with a second mode, the second mode being distinct from the first mode, wherein detecting the change in the gaze of the user is detecting that the gaze of the user has shifted away from the viewing area and is directed at one of the one or more user interface elements.

\* \* \* \* \*

UNITED STATES PATENT AND TRADEMARK OFFICE
CERTIFICATE OF CORRECTION

| | | |
|---|---|---|
| PATENT NO. | : 12,164,684 B2 | Page 1 of 1 |
| APPLICATION NO. | : 18/340701 | |
| DATED | : December 10, 2024 | |
| INVENTOR(S) | : Itkowitz et al. | |

It is certified that error appears in the above-identified patent and that said Letters Patent is hereby corrected as shown below:

In the Specification

Column 5, Line 67, change "system may" to -- system 20 may --

Column 6, Line 2, change "tem also" to -- tem 20 also --

Column 11, Line 51, add -- 30a -- before "and"

Signed and Sealed this
Eleventh Day of February, 2025

Coke Morgan Stewart
*Acting Director of the United States Patent and Trademark Office*